United States Patent
Wang et al.

(10) Patent No.: US 10,330,601 B2
(45) Date of Patent: Jun. 25, 2019

(54) METHOD FOR MOLECULE DETECTION

(71) Applicants: Tsinghua University, Beijing (CN); HON HAI PRECISION INDUSTRY CO., LTD., New Taipei (TW)

(72) Inventors: Ying-Cheng Wang, Beijing (CN); Yuan-Hao Jin, Beijing (CN); Qun-Qing Li, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 16/116,116

(22) Filed: Aug. 29, 2018

(65) Prior Publication Data

US 2019/0079016 A1    Mar. 14, 2019

(30) Foreign Application Priority Data

Sep. 8, 2017 (CN) .......................... 2017 1 0807472

(51) Int. Cl.
| | |
|---|---|
| *G01J 3/44* | (2006.01) |
| *G01N 21/65* | (2006.01) |
| *G01N 21/03* | (2006.01) |
| *G01N 33/487* | (2006.01) |
| *B01L 3/00* | (2006.01) |
| *B82Y 20/00* | (2011.01) |
| *B82Y 30/00* | (2011.01) |
| *B82Y 15/00* | (2011.01) |

(52) U.S. Cl.
CPC ...... *G01N 21/658* (2013.01); *B01L 3/502707* (2013.01); *G01J 3/44* (2013.01); *G01N 21/0303* (2013.01); *G01N 33/48721* (2013.01); *B82Y 15/00* (2013.01); *B82Y 20/00* (2013.01); *B82Y 30/00* (2013.01)

(58) Field of Classification Search
CPC combination set(s) only.
See application file for complete search history.

(56) References Cited

U.S. PATENT DOCUMENTS

2015/0233832 A1*  8/2015  Maruyama ........... G01N 21/658
                                                         356/244

* cited by examiner

*Primary Examiner* — Abdullahi Nur
(74) *Attorney, Agent, or Firm* — ScienBiziP, P.C.

(57) ABSTRACT

The disclosure relates to a method for detecting single molecules on an object. The method includes: providing a carrier; attaching the carrier on a surface of the object so that the surface of the object is indirect contact with the carrier; and detecting the single molecules on the object with a detector. The carrier includes a flexible substrate and a metal layer on the flexible substrate. The flexible substrate includes a base and a bulge pattern located on a surface of the base. The bulge pattern includes a number of strip-shaped bulges intersecting with each other to form a net and define a number of recesses. The metal layer is located on the bulge pattern. The carrier has a relative higher SERS and can enhance the Raman scattering.

20 Claims, 23 Drawing Sheets

METHOD FOR MOLECULE DETECTION

CROSS-REFERENCE TO RELATED APPLICATIONS

This application claims all benefits accruing under 35 U.S.C. § 119 from China Patent Application No. 201710807472.1, filed on Sep. 8, 2017, in the China Intellectual Property Office, the disclosure of which is incorporated herein by reference. This application is related to applications entitled, "CARRIER FOR USE IN SINGLE MOLECULE DETECTION", and "METHOD FOR MAKING CARRIER FOR USE IN SINGLE MOLECULE DETECTION".

BACKGROUND

1. Technical Field

The present disclosure relates to a carrier for use in single molecule detection, a method for making the same, and a method for using the same to detect single molecules.

2. Description of Related Art

Raman spectroscopy is widely used in single molecule detection.

A method for detecting single molecules using Raman spectroscopy is provided. An aggregated silver particle film is coated on a surface of a glass substrate. A number of single molecule samples are disposed on the aggregated silver particle film. A laser irradiation is supplied to the single molecule samples by a Raman detection system to cause a Raman scattering and produce a Raman spectroscopy. The Raman spectroscopy is received by a sensor and analyzed by a computer. However, the substrate for carrying single molecules is usually rigid and made of rigid material such as glass, silicon, silicon dioxide, silicon nitride, quartz, gallium nitride, alumina or magnesium oxide. Thus, the single molecules have to be extracted before the detecting from the object and the object with anomalistic shapes cannot be detected in real time, in situ, on line, or in vivo.

What is needed, therefore, is a carrier for use in single molecule detection that overcomes the problems as discussed above.

Therefore, there is room for improvement within the art.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
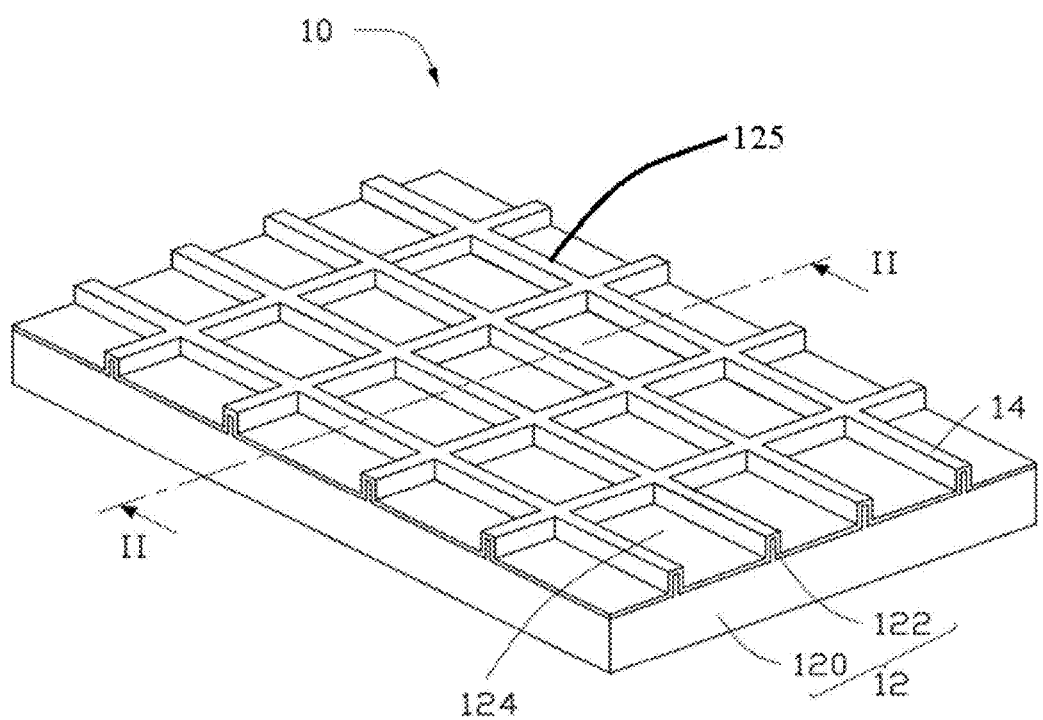
FIG. 1 is a schematic section view of one embodiment of a carrier for use in single molecule detection.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated better illustrate details and features. The description is not to considered as limiting the scope of the embodiments described herein.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

References will now be made to the drawings to describe, in detail, various embodiments of the present carrier for use in single molecule detection, a method for making the same, and a method for using the same to detect single molecules.

Figure 2:
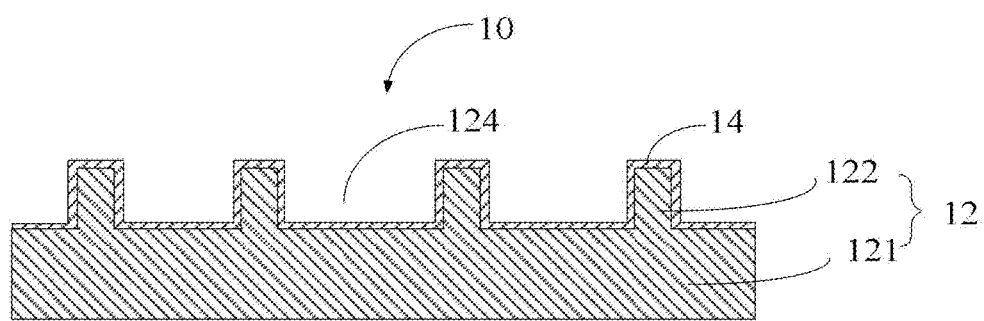
FIG. 2 is a cross-sectional view, along a line II-II of FIG. 1.
Figure 3:
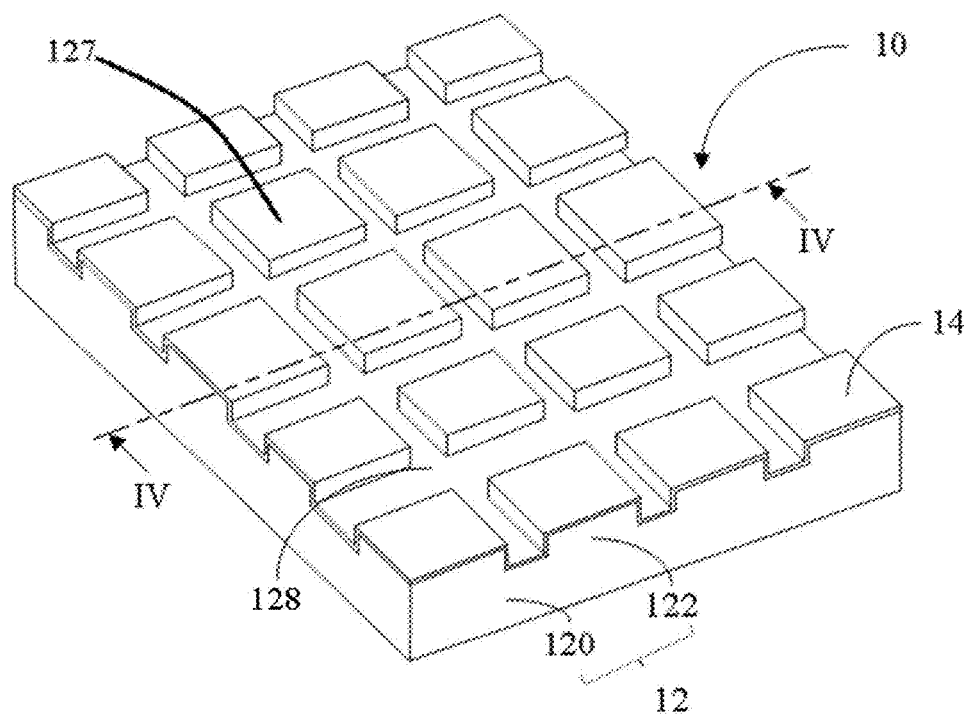
FIG. 3 is a schematic section view of one embodiment of a carrier for use in single molecule detection.
Figure 4:
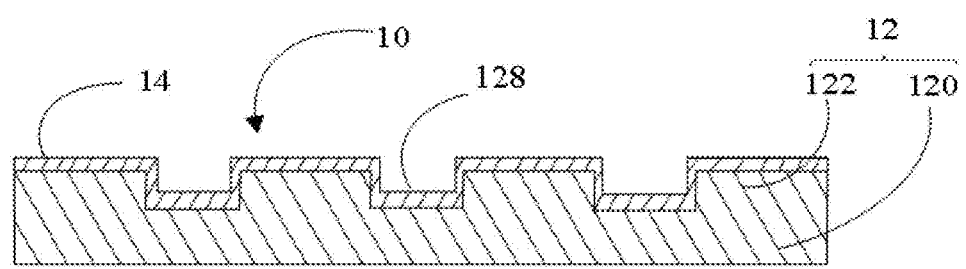
FIG. 4 is a cross-sectional view, along a line IV-IV of FIG. 3.

Referring to FIGS. 1-4, a carrier 10 for use in single molecule detection of one embodiment is provided. The carrier 10 comprises a flexible substrate 12 and a metal layer 14 located on the flexible substrate 12. The flexible substrate 12 comprises a base 120 and a first bulge pattern 122 located on a surface of the base 120. The first bulge pattern 122 can comprise a plurality of strip-shaped bulges 125 intersecting with each other to form a net and define a plurality of first recesses 124 as shown in FIGS. 1-2. The first bulge pattern 122 can also comprise a plurality of block-shaped bulges 127 spaced apart from each other, arranged to form an array, and defines a plurality of grooves 128 as shown in FIGS. 3-4. The plurality of strip-shaped bulges 125 is an intergrated structure. The metal layer 14 is located on surfaces of the first bulge pattern 122. The carrier 10 for use in single molecule detection has a relative higher SERS and can enhance the Raman scattering.

The flexible substrate 12 is transparent and has a light transmittance higher than 75%. In one embodiment, the flexible substrate 12 has a light transmittance higher than 90%. Thus, when a laser passes through the flexible substrate 12 and reaches the metal layer 14, the Raman signal remains strong enough to be detected. In one embodiment, the flexible substrate 12 has a light transmittance higher than 90%. The flexible substrate 12 can be curved and folded into any shape so that the carrier 10 can be attached to a surface of an object with anomalistic shapes. The flexible substrate 12 can be made of a polymer such as polyimide (PI), polydimethylsiloxane (PDMS), or polymethylmethacrylate (PMMA). In one embodiment, the flexible substrate 12 is a polymer. The size and thickness of the flexible substrate 12 can be selected according to need. The thickness of the flexible substrate 12 can range from about 500 nanometers to about 10 millimeters. The thickness of the flexible substrate 12 can range from about 10 micrometers to about 200 micrometers. In one embodiment, the flexible substrate 12 is a PMMA sheet with a thickness of 10 micrometers.

The first bulge pattern 122 and the base 120 can have the same material or different materials. In one embodiment, the first bulge pattern 122 and the base 120 are an intergrated structure. The first bulge pattern 122 can be located on a single surface or two opposite surfaces of the base 120. As shown in FIG. 1, each of the plurality of strip-shaped bulges 125 has a length less than or equal to the width or length of the base 120. The plurality of strip-shaped bulges 125 comprises a plurality of first strip-shaped bulges and a plurality of second strip-shaped bulges. The plurality of first strip-shaped bulges are substantially parallel with each other and extends along the first direction, and the plurality of second strip-shaped bulges are substantially parallel with each other and extends along the second direction different from the first direction. The angle between the first direction and the second direction is greater than 0 degrees an less than or equal to 90 degrees. In one embodiment, the angle between the first direction and the second direction is greater than 30 degrees.

The width of the plurality of strip-shaped bulges 125 can range from about 20 nanometers to about 150 nanometers. In one embodiment, the width of the plurality of strip-shaped bulges 125 can range from about 20 nanometers to about 100 nanometers. In one embodiment, the width of the plurality of strip-shaped bulges 125 can range from about 20 nanometers to about 50 nanometers. The distance between adjacent two of the plurality of strip-shaped bulges 125 can range from about 10 nanometers to about 300 nanometers. In one embodiment, the distance between adjacent two of the plurality of strip-shaped bulges 125 can range from about 10 nanometers to about 100 nanometers. In one embodiment, the distance between adjacent two of the plurality of strip-shaped bulges 125 can range from about 10 nanometers to about 50 nanometers. The height of the plurality of strip-shaped bulges 125 can range from about 50 nanometers to about 1000 nanometers. In one embodiment, the height of the plurality of strip-shaped bulges 125 can range from about 500 nanometers to about 1000 nanometers. The average diameter of the plurality of first recesses 124 can range from about 10 nanometers to about 300 nanometers, and the depth of the plurality of first recesses 124 can range from about 50 nanometers to about 1000 nanometers. In one embodiment, the ratio between the depth and the average diameter is greater than 5. In one embodiment, the ratio between the depth and the average diameter is greater than 10.

The metal layer 14 can be located on both top and side surfaces of the plurality of strip-shaped bulges 125 and bottom surfaces of the plurality of first recesses 124. The metal layer 14 can be a continuous structure and covers the entire surface of the flexible substrate 12. The metal layer 14 can also be a discontinuous structure. The metal layer 14 can be a single-layer or a multi-layer structure. The thickness of the metal layer 14 can range from about 2 nanometers to about 200 nanometers. The material of the metal layer 14 can be gold, silver, copper, iron, nickel, aluminum, or any alloy thereof. The metal layer 14 can be uniformly deposited on the surface of the flexible substrate 12 by a method of electron beam evaporation, chemical vapor deposition (CVD), or sputtering. In one embodiment, the metal layer 14 is a gold layer with a thickness of about 10 nanometers.

The carrier 10 has following advantages. The carrier 10 can be attached on an irregular surface because of the flexible substrate 12. Thus, the in situ detection can be performed directly on the object. The width and distance of the plurality of strip-shaped bulges 125 are also tens of nanometers, and the average diameter of the plurality of recesses 124 are also tens of nanometers. The density of the strip-shaped bulges 125 and the recesses 124 would be increased. For example, when both the width and distance of the plurality of strip-shaped bulges 125 are 20 nanometers, the number of the strip-shaped bulges 125 and the recesses 124 would be 50 within 1 micrometer. Due to resolution limitations, conventional photolithography methods cannot make all the strip-shaped bulges in nano-scale and obtain this density. At the gap between two adjacent the plurality of strip-shaped bulges 125, a surface plasmon resonance (SPR) is produced on a surface of the metal layer 14 so that the surface-enhanced Raman scattering (SERS) of the carrier 10 will be enhanced. The enhancement factor of SERS of the carrier 10 can range from about $10^5$ to about $10^{15}$. In one embodiment, the enhancement factor of SERS of the carrier 10 is about $10^{10}$.

Figure 5:
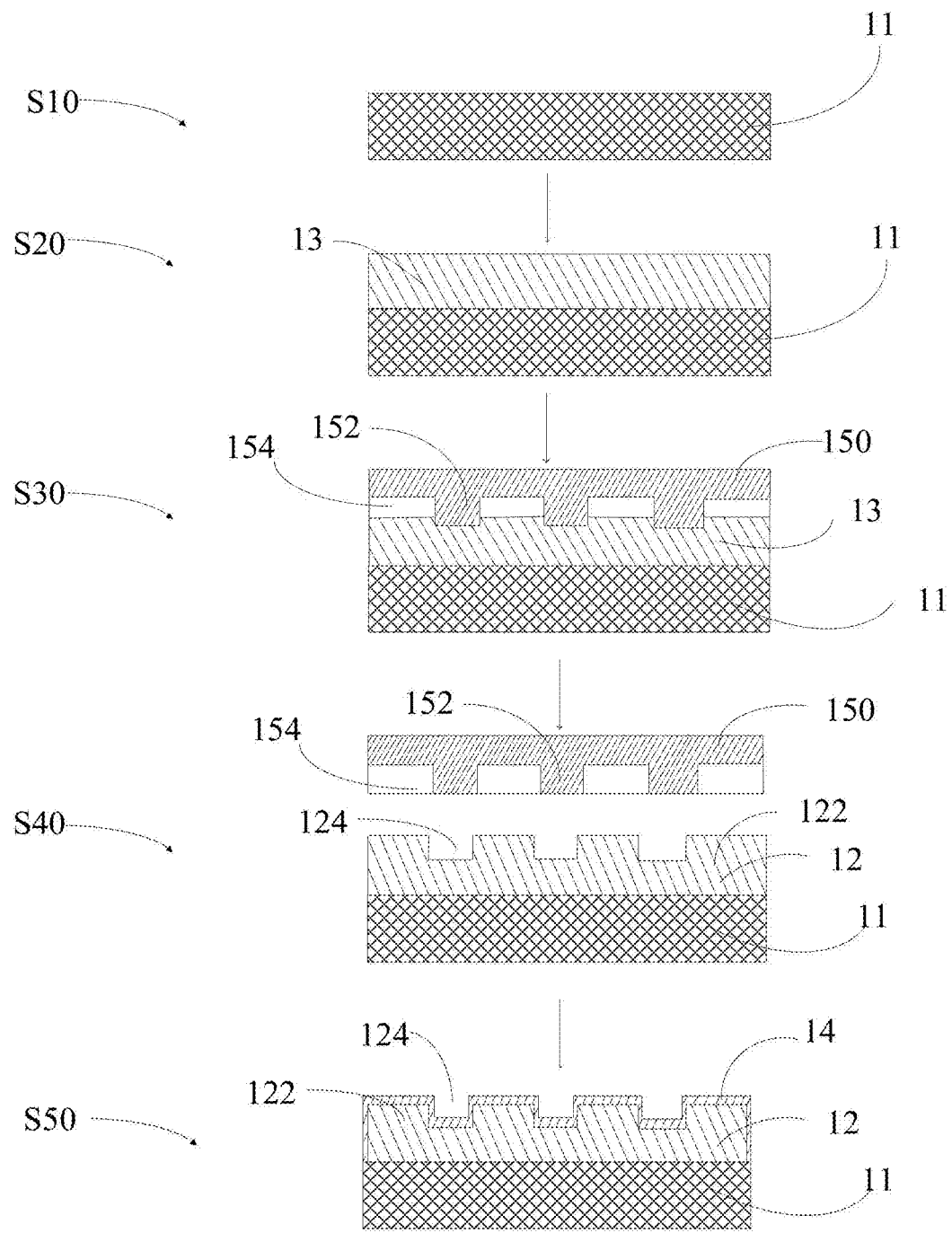
FIG. 5 is a flowchart of one embodiment of a method for making the carriers for use in single molecule detection of FIGS. 1-4.

Referring to FIG. 5, a method for making the carrier 10 may include the following steps:

step (S10), providing a rigid substrate 11;

step (S20), coating a polymer layer 13 on a surface of the rigid substrate 11, wherein the polymer layer 13 is in semisolid state;

step (S30), transferring a nano-scaled pattern of a template 150 on a surface of the polymer layer 13 by pressing the template 150 on the surface of the polymer layer 13;

step (S40), obtaining the flexible substrate 12 by removing the template 150; and step (S50), applying the metal layer 14 on the flexible substrate 12.

In step (S10), the rigid substrate 11 supports the polymer layer 13. The rigid substrate 11 can be a conductive substrate, an insulative substrate, or a semiconductor substrate. The rigid substrate 11 can include metal such as gold, aluminum, nickel, chromium, copper. The rigid substrate 11 can include insulative material such as glass, quartz, silicon dioxide ($SiO_2$), or silicon nitride ($Si_3N_4$), alumina ($Al_2O_3$), magnesia (MgO). The rigid substrate 11 can include semiconductor material such as silicon (Si), gallium nitride (GaN), or gallium arsenide (GaAs). The size and thickness of the rigid substrate 11 can be selected according to need. In one embodiment, the rigid substrate 11 is a silicon dioxide layer with a thickness of about 0.5 millimeters to 1.2 millimeters.

In step (S20), the material of the polymer layer 13 is can be imprinted at room temperature, has good structural stability and high resolution of 10 nanometers. The material of the polymer layer 13 can be PMMA, PI, or PDMS. In one embodiment, the material of the polymer layer 13 is PMMA backed into semisolid state at low temperature so that the polymer layer 13 has fluidity.

The polymer layer 13 can be formed by spin coating or droplet coating. The thickness of the polymer layer 13 can range from about 500 nanometers to 10 millimeters. The thickness of the polymer layer 13 can range from about 800 nanometers to 5 millimeters. The thickness of the polymer layer 13 can range from about 20 micrometers to 90 micrometers. In one embodiment, the polymer layer 13 is 50 micrometers may be made by following steps:

step (201), providing a PMMA solution;

step (202), spin coating the PMMA solution on a surface of the rigid substrate 11 to form a PMMA coating, the rotating speed ranges from about 500 rpm to about 6000 rpm, the spin coating time ranges from about 0.5 minutes to about 1.5 minutes;

step (203), baking the PMMA coating into semisolid state at low temperature below 50 degrees Celsius for about 3 minutes to about 5 minutes.

In step (S30), the template 150 includes a second bulge pattern 152 includes a plurality of second strip-shaped bulges intersecting with each other to form a net and define a plurality of second recesses 154. The template 150 is made of rigid material such as nickel, silicon, and silicon dioxide. In one embodiment, the template 150 is made of silicon dioxide. When the template 150 is pressed on the polymer layer 13, the polymer layer 13 is filled in the plurality of second recesses 154 of the template 150. The width of the Referring to FIG. 6, a method for making the template 150 may include the following steps:

step (S301), providing a second substrate 15;

step (S302), providing a carbon nanotube structure 110, wherein the carbon nanotube structure 110 includes a plurality of intersecting carbon nanotubes and defines a plurality of openings 116;

step (S303), placing the carbon nanotube structure 110 on a surface 151 of the second substrate 15, wherein parts of the surface 151 are exposed from the plurality of openings 116;

step (S304), forming the second bulge pattern 152 on the surface 151 by dry etching the surface 151 using the carbon nanotube structure 110 as a first mask, wherein the second bulge pattern 152 includes a plurality of second strip-shaped bulges intersecting with each other; and step (S305), removing the carbon nanotube structure 110.

In step (S301), the material of the second substrate 15 is not limited and can be metal, insulating material or semiconductor. The metal can be gold, aluminum, nickel, chromium, or copper. The insulating material can be silicon dioxide or silicon nitride. The semiconductor can be silicon, gallium nitride, or gallium arsenide. In one embodiment, the material of the second substrate 15 is a gallium nitride layer with a thickness of 300 micrometers.

Figure 7:
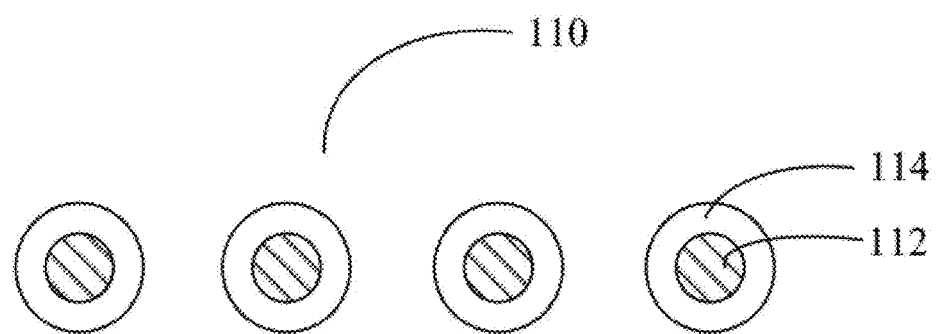
FIG. 7 is a cross-sectional view along line VII-VII of a carbon nanotube structure of FIG. 6

In step (S302), the carbon nanotube structure 110 can be a composite or a pure carbon nanotube structure. In one embodiment, the carbon nanotube structure 110 is a composite including a pure carbon nanotube structure 112 and a protective layer 114 coated on the carbon nanotube structure 112 as shown in FIG. 7. The carbon nanotube structure 112 is a free-standing structure. The term "free-standing structure" includes that the carbon nanotube structure 112 can sustain the weight of itself when it is hoisted by a portion thereof without any significant damage to its structural integrity. Thus, the carbon nanotube structure 112 can be suspended by two spaced supports.

The plurality of carbon nanotubes can be single-walled carbon nanotubes, double-walled carbon nanotubes, or multi-walled carbon nanotubes. The length and diameter of the plurality of carbon nanotubes can be selected according to need. The diameter of the single-walled carbon nanotubes can range from about 0.5 nanometers to about 10 nanometers. The diameter of the double-walled carbon nanotubes can range from about 1.0 nanometer to about 15 nanometers. The diameter of the multi-walled carbon nanotubes can range from about 1.5 nanometers to about 50 nanometers. In one embodiment, the length of the carbon nanotubes can range from about 200 micrometers to about 900 micrometers.

The plurality of carbon nanotubes are orderly arranged to form an ordered carbon nanotube structure. The plurality of carbon nanotubes extend along a direction substantially parallel to the surface of the carbon nanotube structure 112. The term 'ordered carbon nanotube structure' includes, but is not limited to, a structure wherein the plurality of carbon nanotubes are arranged in a consistently systematic manner, e.g., the plurality of carbon nanotubes are arranged approximately along the same direction.

The carbon nanotube structure 112 defines a plurality of apertures. The aperture extends throughout the carbon nanotube structure 112 along the thickness direction thereof. The aperture can be a hole defined by several adjacent carbon nanotubes, or a gap defined by two substantially parallel carbon nanotubes and extending along axial direction of the carbon nanotubes. The hole shaped aperture and the gap shaped aperture can exist in the carbon nanotube structure 112 at the same time. Hereafter, the size of the aperture is the diameter of the hole or width of the gap. The sizes of the apertures can be different. The average size of the apertures can range from about 10 nanometers to about 500 micrometers. For example, the sizes of the apertures can be about 50 nanometers, 100 nanometers, 500 nanometers, 1 micrometer, 10 micrometers, 80 micrometers, or 120 micrometers.

The carbon nanotube structure 112 can include at least one carbon nanotube film, at least one carbon nanotube wire, or combination thereof. In one embodiment, the carbon nanotube structure 112 can include a single carbon nanotube film or two or more carbon nanotube films stacked together. Thus, the thickness of the carbon nanotube structure 112 can be controlled by the number of the stacked carbon nanotube films. The number of the stacked carbon nanotube films can range from about 2 to about 100. For example, the number of the stacked carbon nanotube films can be 10, 30, or 50. In one embodiment, the carbon nanotube structure 112 is formed by folding a single carbon nanotube wire. In one embodiment, the carbon nanotube structure 112 can include a layer of parallel and spaced carbon nanotube wires. Also, the carbon nanotube structure 112 can include a plurality of carbon nanotube wires intersecting or weaved together to form a carbon nanotube net. The distance between two adjacent parallel and spaced carbon nanotube wires can range from about 0.1 micrometers to about 200 micrometers. In one embodiment, the distance between two adjacent parallel and spaced carbon nanotube wires ranges from about 10 micrometers to about 100 micrometers. The gap between two adjacent substantially parallel carbon nanotube wires is defined as the apertures. The size of the apertures can be controlled by controlling the distance between two adjacent parallel and spaced carbon nanotube wires. The length of the gap between two adjacent parallel carbon nanotube wires can be equal to the length of the carbon nanotube wire. It is understood that any carbon nanotube structure described can be used with all embodiments.

Figure 8:
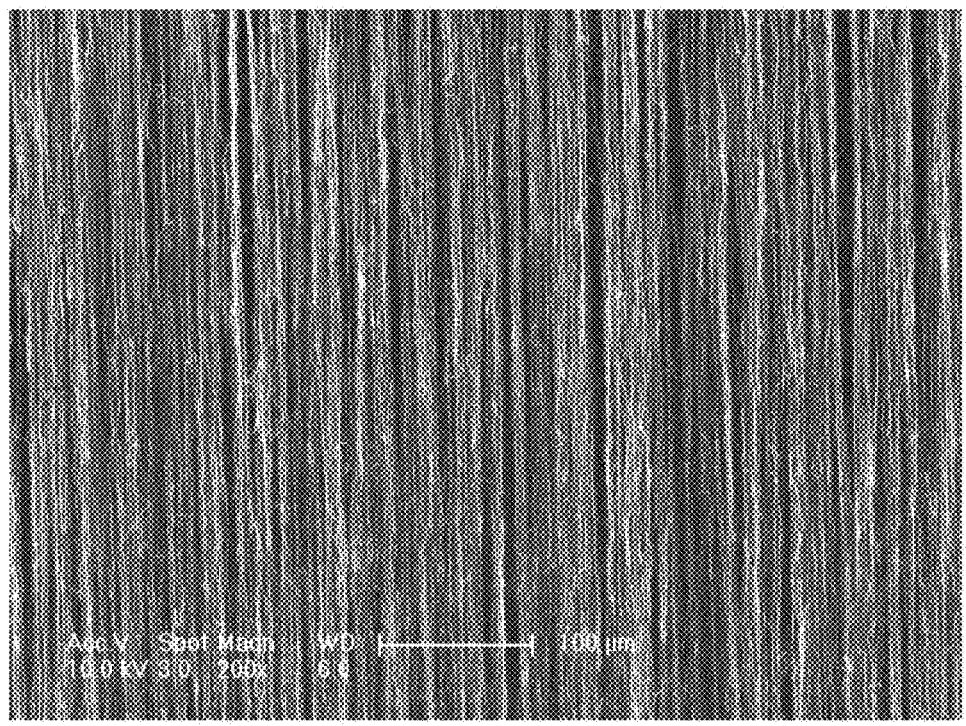
FIG. 8 is a Scanning Electron Microscope (SEM) of a drawn carbon nanotube film of one embodiment.

In one embodiment, the carbon nanotube structure 112 includes at least one drawn carbon nanotube film. The drawn carbon nanotube film can be drawn from a carbon nanotube array that is able to have a film drawn therefrom. The drawn carbon nanotube film includes a plurality of successive and oriented carbon nanotubes joined end-to-end by van der Waals attractive force therebetween. The drawn carbon nanotube film is a free-standing film. Referring to FIG. 8, each drawn carbon nanotube film includes a plurality of successively oriented carbon nanotube segments joined end-to-end by van der Waals attractive force therebetween. Each carbon nanotube segment includes a plurality of carbon nanotubes parallel to each other, and combined by van der Waals attractive force therebetween. As can be seen in FIG. 8, some variations can occur in the drawn carbon nanotube film. The carbon nanotubes in the drawn carbon nanotube film are oriented along a preferred orientation. The drawn carbon nanotube film can be treated with an organic solvent to increase the mechanical strength and toughness and reduce the coefficient of friction of the drawn carbon nanotube film. A thickness of the drawn carbon nanotube film can range from about 0.5 nanometers to about 100 micrometers. The drawn carbon nanotube film defines a plurality of apertures between adjacent carbon nanotubes.

The carbon nanotube structure 112 can include at least two stacked drawn carbon nanotube films. In other embodiments, the carbon nanotube structure 112 can include two or more coplanar carbon nanotube films, and can include layers of coplanar carbon nanotube films. Additionally, when the carbon nanotubes in the carbon nanotube film are aligned along one preferred orientation (e.g., the drawn carbon nanotube film), an angle can exist between the orientation of carbon nanotubes in adjacent films, whether stacked or adjacent. Adjacent carbon nanotube films can be combined by only the van der Waals attractive force therebetween. An angle between the aligned directions of the carbon nanotubes in two adjacent carbon nanotube films can range from about 0 degrees to about 90 degrees. When the angle between the aligned directions of the carbon nanotubes in adjacent stacked drawn carbon nanotube films is larger than 0 degrees, a plurality of micropores is defined by the carbon nanotube structure 112. In one embodiment, the carbon nanotube structure 112 has the aligned directions of the carbon nanotubes between adjacent stacked drawn carbon nanotube films at 90 degrees. Stacking the carbon nanotube films will also add to the structural integrity of the carbon nanotube structure 112.

Figure 9:
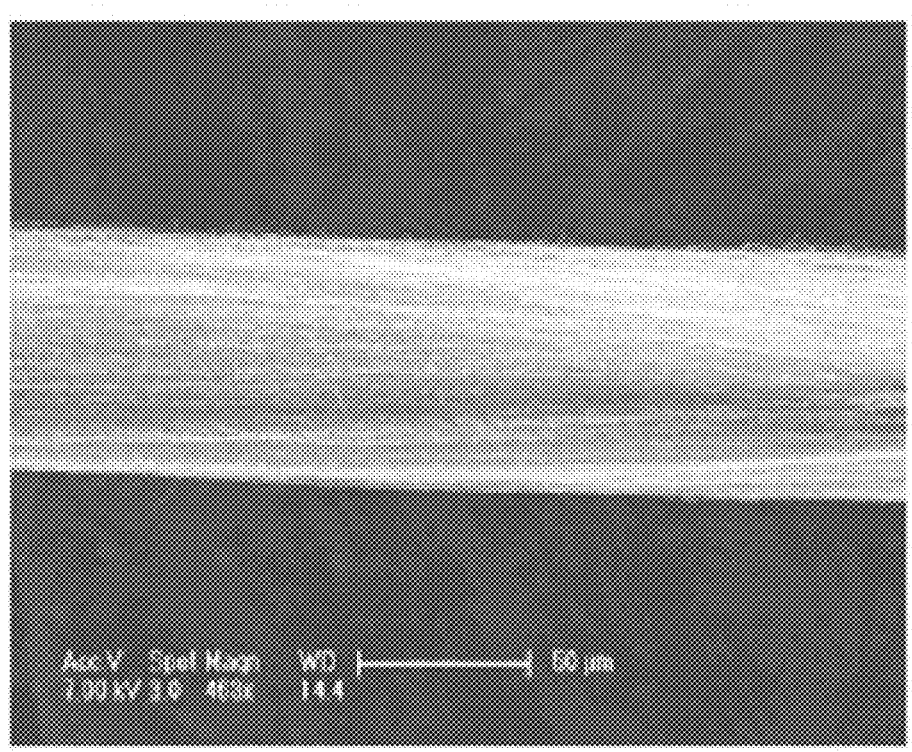
FIG. 9 is an SEM image of an untwisted carbon nanotube wire of one embodiment.

The carbon nanotube wire can be untwisted or twisted. Treating the drawn carbon nanotube film with a volatile organic solvent can form the untwisted carbon nanotube wire. Specifically, the organic solvent is applied to soak the entire surface of the drawn carbon nanotube film. During the soaking, adjacent parallel carbon nanotubes in the drawn carbon nanotube film will bundle together, due to the surface tension of the organic solvent as it volatilizes, and thus, the drawn carbon nanotube film will be shrunk into an untwisted carbon nanotube wire. Referring to FIG. 9, the untwisted carbon nanotube wire includes a plurality of carbon nanotubes substantially oriented along the same direction (i.e., a direction along the length of the untwisted carbon nanotube wire). The carbon nanotubes are substantially parallel to the axis of the untwisted carbon nanotube wire. More specifically, the untwisted carbon nanotube wire includes a plurality of successive carbon nanotube segments joined end to end by van der Waals attractive force therebetween. Each carbon nanotube segment includes a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire ranges from about 0.5 nanometers to about 100 micrometers.

Figure 10:
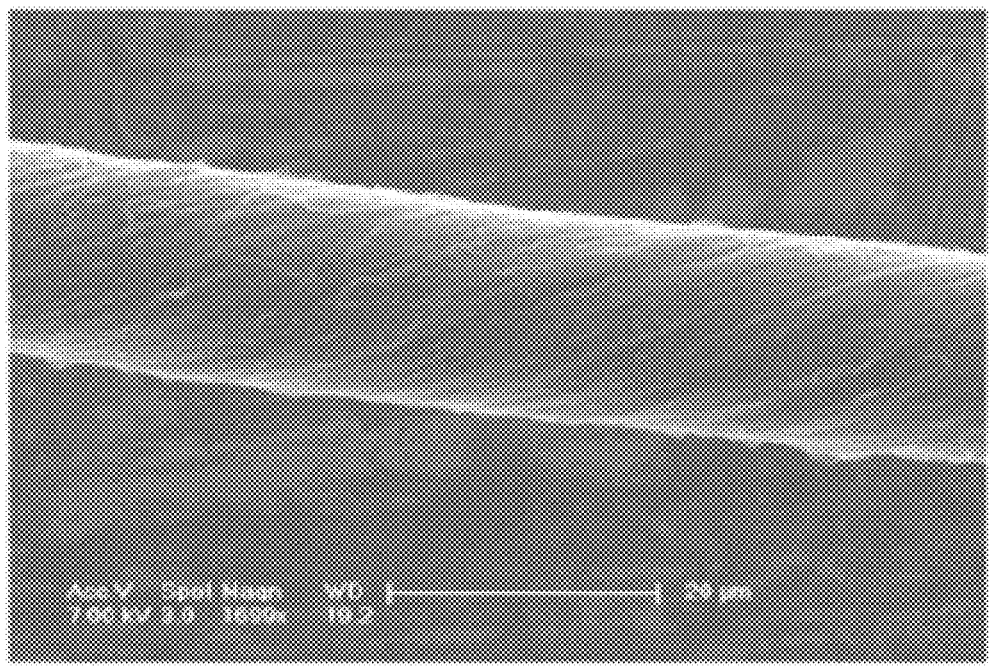
FIG. 10 is an SEM image of a twisted carbon nanotube wire of one embodiment.

The twisted carbon nanotube wire can be formed by twisting a drawn carbon nanotube film using a mechanical force to turn the two ends of the drawn carbon nanotube film in opposite directions. Referring to FIG. 10, the twisted carbon nanotube wire includes a plurality of carbon nanotubes helically oriented around an axial direction of the twisted carbon nanotube wire. More specifically, the twisted carbon nanotube wire includes a plurality of successive carbon nanotube segments joined end to end by van der Waals attractive force therebetween. Each carbon nanotube segment includes a plurality of carbon nanotubes parallel to each other, and combined by van der Waals attractive force therebetween. The length of the carbon nanotube wire can be set as desired. A diameter of the twisted carbon nanotube wire can be from about 0.5 nanometers to about 100 micrometers. Further, the twisted carbon nanotube wire can be treated with a volatile organic solvent after being twisted to bundle the adjacent paralleled carbon nanotubes together. The specific surface area of the twisted carbon nanotube wire will decrease, while the density and strength of the twisted carbon nanotube wire will increase.

The carbon nanotube structure 110 can be made by applying a protective layer 114 on a surface of the carbon nanotube structure 112. The carbon nanotube structure 112 can be suspended in a depositing chamber during depositing the protective layer 114 so that two opposite surfaces of the carbon nanotube structure 112 are coated with the protective layer 114. In some embodiments, each of the plurality of carbon nanotubes is fully enclosed by the protective layer 114. In one embodiment, the carbon nanotube structure 112 is located on a frame so that the middle portion of the carbon nanotube structure 112 is suspended through the through hole of the frame. The frame can be any shape, such as a quadrilateral. The carbon nanotube structure 112 can also be suspended by a metal mesh or metal ring.

The method of depositing the protective layer 114 can be physical vapor deposition (PVD), chemical vapor deposition (CVD), atomic layer deposition (ALD), magnetron sputtering, or spraying.

The plurality of openings 116 are formed because of the plurality of apertures of the carbon nanotube structure 112. The plurality of openings 116 and the plurality of apertures have the same shape and different size. The size of the plurality of openings 116 is smaller than that of the plurality of apertures because the protective layer 114 is deposited in the plurality of apertures.

The thickness of the protective layer 114 ranges from about 3 nanometers to about 50 nanometers. In one embodiment, the thickness of the protective layer 114 ranges from about 3 nanometers to about 20 nanometers. If the thickness of the protective layer 114 is less than 3 nanometers, the protective layer 114 cannot prevent the carbon nanotubes from being destroyed in following etching process. If the thickness of the protective layer 114 is greater than 50 nanometers, the plurality of apertures may be fully filled by the protective layer 114 and the plurality of openings 116 cannot be obtained.

The material of the protective layer 114 can be metal, metal oxide, metal nitride, metal carbide, metal sulfide, silicon oxide, silicon nitride, or silicon carbide. The metal can be gold, nickel, titanium, iron, aluminum, titanium, chromium, or alloy thereof. The metal oxide can be alumina, magnesium oxide, zinc oxide, or hafnium oxide. The material of the protective layer 114 is not limited above and can be any material as long as the material can be deposited on the carbon nanotube structure 112, would not react with the carbon nanotubes and would not be etched easily in following drying etching process. The protective layer 114 is combined with the carbon nanotube structure 112 by van der Waals attractive force therebetween only.

Figure 11:
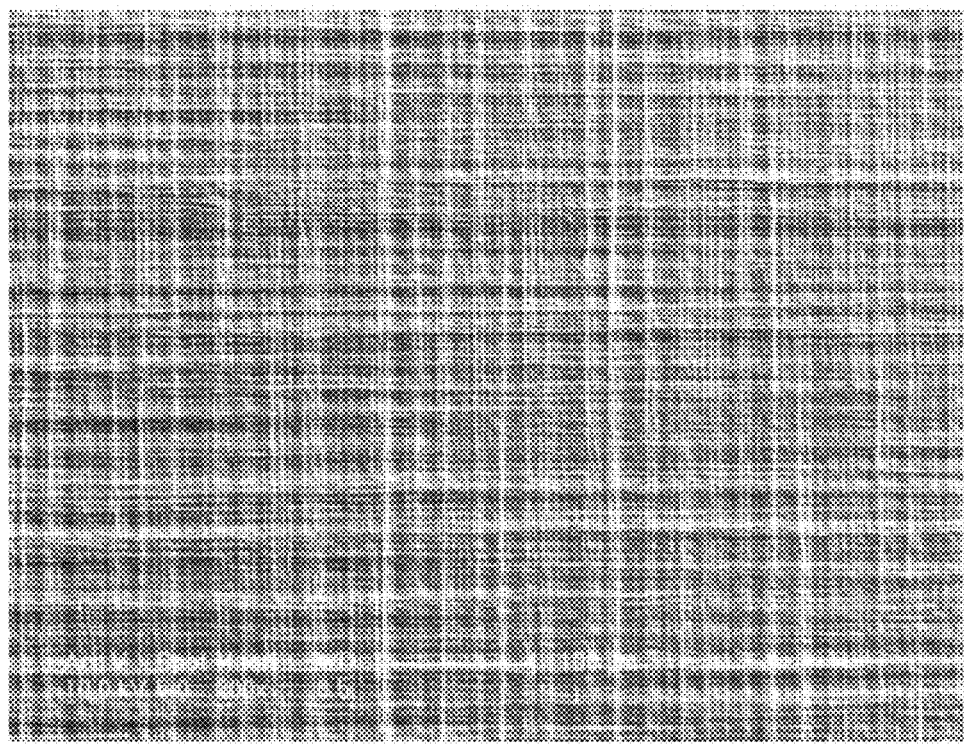
FIG. 11 is an SEM image of a carbon nanotube structure of one embodiment.
Figure 12:
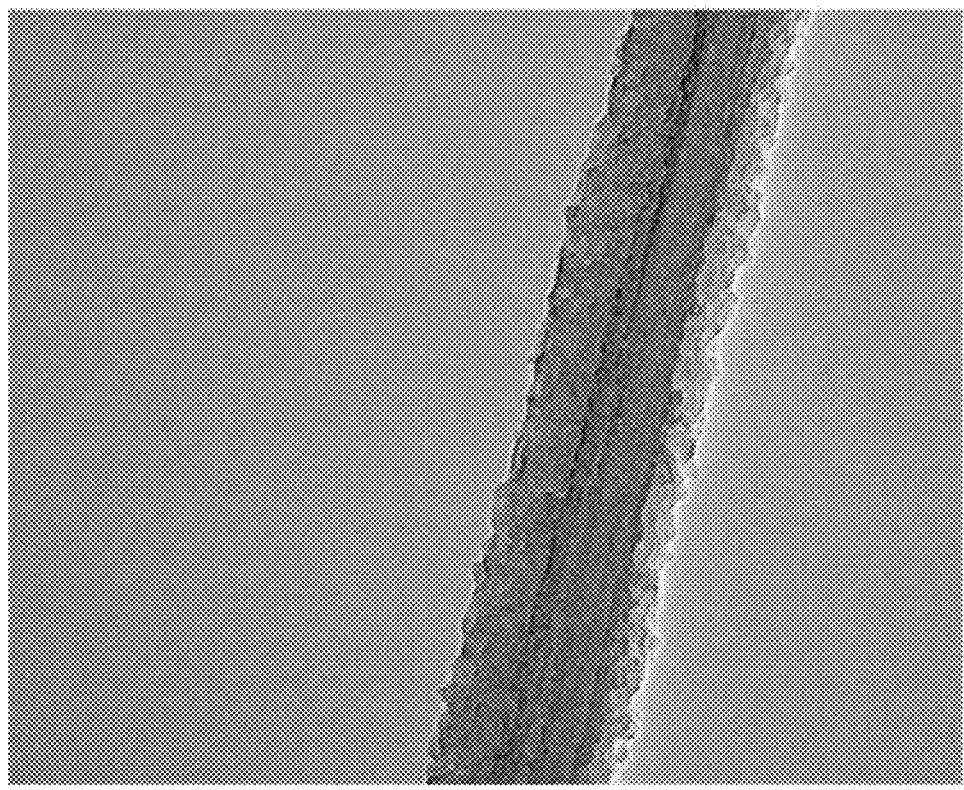
FIG. 12 is an SEM image of a single carbon nanotube coated with an alumina ($Al_2O_3$) layer.

As shown in FIG. 11, in one embodiment, an alumina layer of 5 nanometers thickness is deposited on two stacked drawn carbon nanotube films by electron beam evaporation. As shown in FIG. 12, each of the carbon nanotubes is entirely coated by the alumina layer. The aligned direction of the carbon nanotubes between adjacent stacked drawn carbon nanotube films is 90 degrees.

In step (S303), the carbon nanotube structure 110 can be in direct contact with the surface 151 of the second substrate 15 or suspended above the surface 151 of the second substrate 15 by a support. In one embodiment, the carbon nanotube structure 110 is transferred on the surface 151 of the second substrate 15 through the frame.

In one embodiment, the placing the carbon nanotube structure 110 on the surface 151 further comprises solvent treating the second substrate 15 with the carbon nanotube structure 110 thereon. Because there is air between the carbon nanotube structure 110 and the surface 151 of the second substrate 15, the solvent treating can exhaust the air and allow the carbon nanotube structure 110 to be closely and firmly adhered on the surface 151 of the second substrate 15. The solvent treating can be applying a solvent to entire surface of the carbon nanotube structure 110 or immersing the entire second substrate 15 with the carbon nanotube structure 110 in a solvent. The solvent can be water or volatile organic solvent such as ethanol, methanol, acetone, dichloroethane, chloroform, or mixtures thereof. In one embodiment, the organic solvent is ethanol.

In the step (S304), the dry etching can be plasma etching or reactive ion etching (RIE). In one embodiment, the dry etching is performed by applying plasma energy on the entire or part surface of the surface 151 via a plasma device. The plasma gas can be an inert gas and/or etching gases, such as argon (Ar), helium (He), chlorine ($Cl_2$), hydrogen ($H_2$), oxygen ($O_2$), fluorocarbon ($CF_4$), ammonia ($NH_3$), or air.

In one embodiment, the plasma gas is a mixture of chlorine and argon. The power of the plasma device can range from about 20 watts to about 70 watts. The plasma flow of chlorine can range from about 5 sccm to about 20 sccm, such as 10 sccm. The plasma flow of argon can range from about 15 sccm to about 40 sccm, such as 25 sccm. When the plasma is produced in vacuum, the work pressure of the plasma can range from about 3 Pa to 10 Pa, such as 6 Pa. The time for plasma etching can range from about 10 seconds to about 20 seconds, such as 15 seconds.

In the plasma etching process, the plasma gas would react with the exposed portion of the second substrate 15 and would not react with the protective layer 114, or reaction between the plasma gas and the protective layer 114 is much slower than reaction between the plasma gas and the second substrate 15. The selection relationship of the plasma gas, material of the second substrate 15 and material of the protective layer 114 is shown in Table 1 below.

TABLE 1

| Number | Substrate | protective layer | Plasma gas |
|---|---|---|---|
| 1 | Al | $SiO_2$ | $Cl_2$ or $BCl_3$ |
| 2 | $SiO_2$ | Al, Cr, Fe, Ti, Ni, or Au | $CF_4$ |
| 3 | $SiN_x$ | Al, Cr, Fe, Ti, Ni, or Au | $CF_4$ |
| 4 | GaN | $Al_2O_3$ | $Cl_2$ or $Ar_2$ |
| 5 | Au, Cr or Ni | $SiO_2$ or $SiN_x$ | $O_2$ or $Ar_2$ |
| 6 | Cu | $SiO_2$ or $SiN_x$ | $O_2$ or $BCl_3$ |

In the etching process, the etching gas reacts with the second substrate 15, but does not react with the protective layer 114 or react with the protective layer 114 at a speed much less than that of the reaction between the etching gas and the second substrate 15. Thus, the exposed portion of the second substrate 15 would be etched gradually and the portion of the second substrate 15 that are shielded by the carbon nanotube structure 110 would not be etched.

Figure 6:
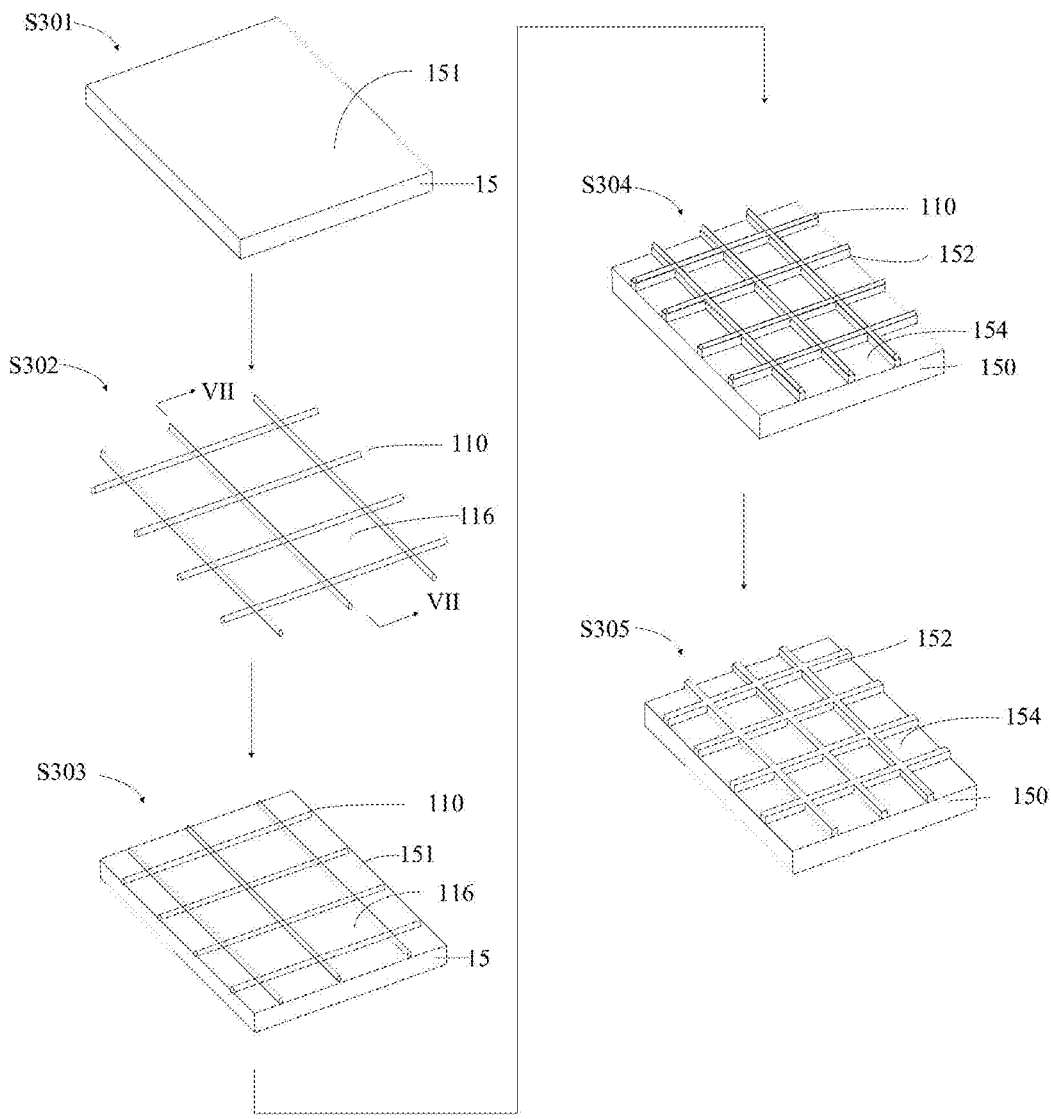
FIG. 6 is a flowchart of one embodiment of a method for making a template.

The bulge pattern 152 and the carbon nanotube structure 110 substantially have the same pattern. When the carbon nanotube structure 112 includes a plurality of intersecting drawn carbon nanotube films, the bulge pattern 152 includes a plurality of strip-shaped bulges intersecting with each other to form a net structure as shown in FIG. 6.

The plurality of strip-shaped bulges can have a width ranges from about 20 nanometers to about 150 nanometers, a distance ranges from about 10 nanometers to about 300 nanometers, and a height ranges from about 50 nanometers to about 1000 nanometers.

After coating with the protective layer 114, the diameter of the carbon nanotubes are about tens of nanometers, and distance between adjacent two carbon nanotubes are about tens of nanometers. Thus, the width and distance of the plurality of strip-shaped bulges are also tens of nanometers, and the average diameter of the plurality of hole are also tens of nanometers. The density of the strip-shaped bulges and the hole would be increased. For example, when both the width and distance of the plurality of strip-shaped bulges are 20 nanometers, the number of the strip-shaped bulges and the hole would be 50 within 1 micrometer. The conventional photolithography method cannot make all the strip-shaped bulges in nano-scale and obtain this density due to the resolution limitation. At the gap between two adjacent the plurality of strip-shaped bulges, a surface plasmon resonance (SPR) is produced on a surface of the metal layer 14 so that the surface-enhanced Raman scattering (SERS) of the carrier 10 will be outstandingly enhanced. The enhancement factor of SERS of the carrier 10 ranges from about $10^5$ to about $10^{15}$. In one embodiment, the enhancement factor of SERS of the carrier 10 is about $10^{10}$.

In step (S305), the method of removing the carbon nanotube structure 110 can be ultrasonic method, or adhesive tape peeling, oxidation. In one embodiment, the second substrate 15 with the carbon nanotube structure 110 thereon is placed in an N-methyl pyrrolidone solution and ultrasonic treating for several minutes.

Alternatively, a method for making the template 150 may include the following steps:

step (S301'), providing a second substrate 15;

step (S302'), providing a carbon nanotube structure 110, wherein the carbon nanotube structure 110 includes a plurality of intersecting carbon nanotubes and defines a plurality of openings 116;

step (S303'), placing the carbon nanotube structure 110 on a surface 151 of the second substrate 15, wherein parts of the surface 151 are exposed from the plurality of openings 116;

step (S304'), depositing a second mask layer on the surface 151 to cover the carbon nanotube structure 110, wherein the second mask includes oxides such as $SiO_2$, hafnium oxide, alumina, or other oxides;

step (S305'), obtaining a second mask by removing the carbon nanotube structure 110, the second mask includes a plurality of openings intersecting with each other to expose part of the surface 151;

step (S306'), forming the second bulge pattern 152 on the surface 151 by dry etching the surface 151 using the second mask, wherein the second bulge pattern 152 includes block-shaped bulges spaced apart from each other, arranged to form an array, and defines a plurality of grooves; and step (S307'), removing the second mask.

The flexible substrate 12 is formed by nanoimprinting the polymer layer 13. In one embodiment, the PMMA coating is baked to form the polymer layer 13 in semisolid state in a vacuum room with a pressure $1 \times 10^{-1}$ mbar-$1 \times 10^{-5}$ mbar first, and then the polymer layer 13 is nanoimprinted by pressing the template 150 using a force ranges from about 2 pounds per square inch (Psi) to about 100 Psi for about 2 minutes to about 30 minutes. Then, the template 150 is separated from the polymer layer 13.

The first bulge pattern 122 is formed on the polymer layer 13. The first bulge pattern 122 comprise a plurality of strip-shaped bulges 125 intersecting with each other to form a net and define a plurality of first recesses 124. The plurality of strip-shaped bulges 125 corresponds the plurality of second recesses 154. The width of the plurality of first recesses 124 ranges from about 20 nanometers to about 200 nanometers, and the width of the plurality of strip-shaped bulges 125 ranges from about 30 nanometers to about 300 nanometers.

In step (S40), the temperate 150 can be removed by applying a mechanical force or etching. After removing the temperate 150, the polymer layer 13 can be further baked for about 3 minutes to about 5 minutes at a temperature ranges from about 120 degrees Celsius to about 180 degrees Celsius so that a free standing flexible substrate 12 can be obtained.

In step (S50), the metal layer 14 can be deposited on the first bulge pattern 122 by a method of electron beam evaporation, ion beam sputtering, atomic layer deposition, magnetron sputtering, thermal vapor deposition, or chemical vapor deposition. The thickness of the metal layer 14 can range from about 2 nanometers to about 200 nanometers. The material of the metal layer 14 can be gold, silver, copper, iron, nickel, aluminum or alloy thereof. In one embodiment, the metal layer 14 is a gold layer with a thickness of about 10 nanometers. The gold layer covers entire surfaces of the first bulge pattern 122. The gold layer is in direct contact with the bottom surfaces of the hole.

Figure 13:
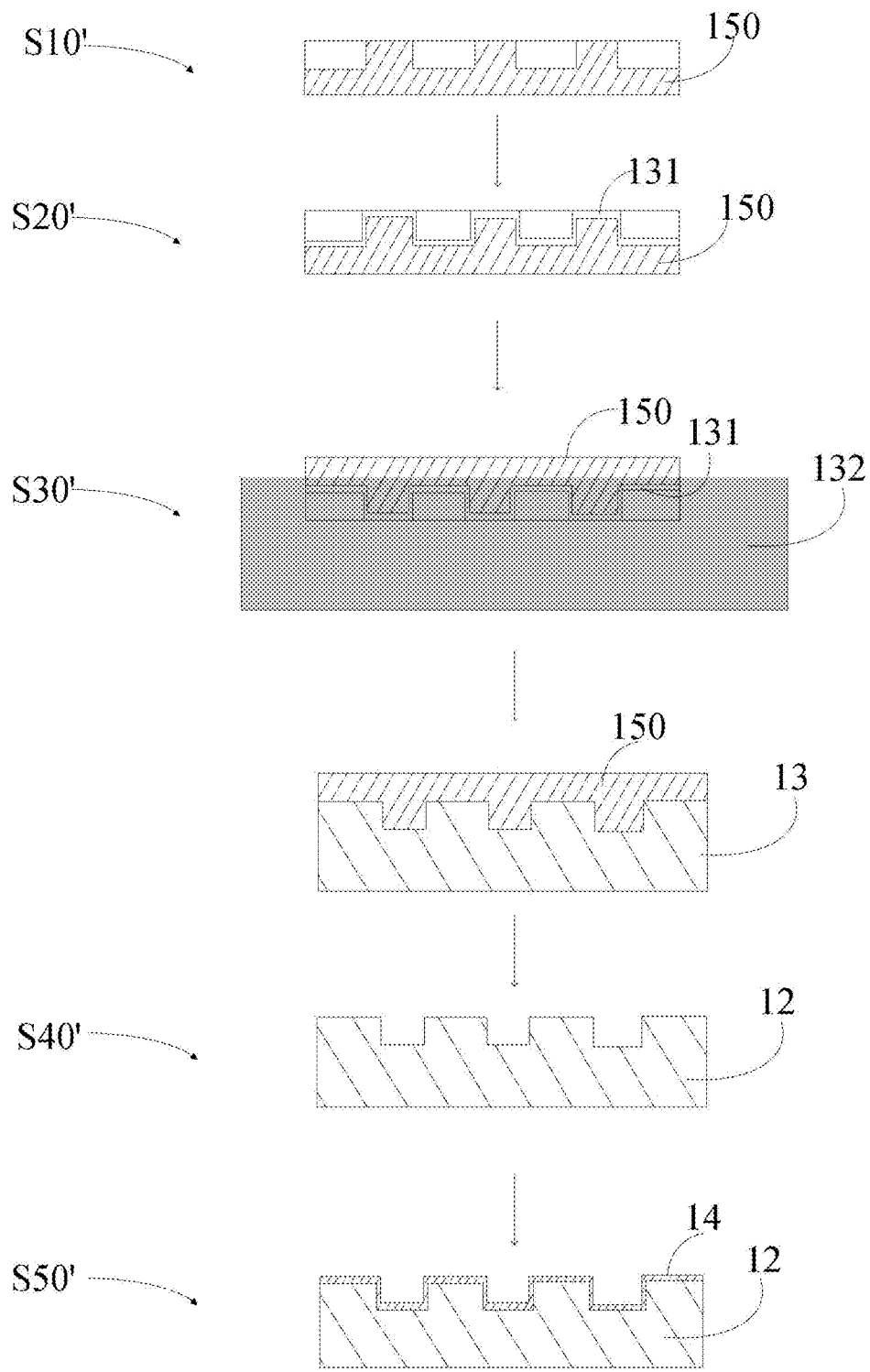
FIG. 13 is a flowchart of another embodiment of a method for making the carriers for use in single molecule detection of FIGS. 1-4.

Referring to FIG. 13, a method for making the carrier 10 of another embodiment may include the following steps:

step (S10'), providing a template 150, wherein the template 150 comprises a second bulge pattern 152;

step (S20'), coating an evocating agent layer 131 on the bulge pattern 152;

step (S30'), immersing the agent layer 131 in a monomer solution 132 so that a polymer layer 13 is formed on the bulge pattern 152;

step (S40'), obtaining the flexible substrate 12 by removing the template 150; and step (S50'), applying the metal layer 14 on the flexible substrate 12.

In the method of FIG. 13, the polymer layer 13 is formed by a polymerization of the monomer solution 132. Thus, the polymer layer 13 can have the same pattern of the bulge pattern 152.

Figure 14:
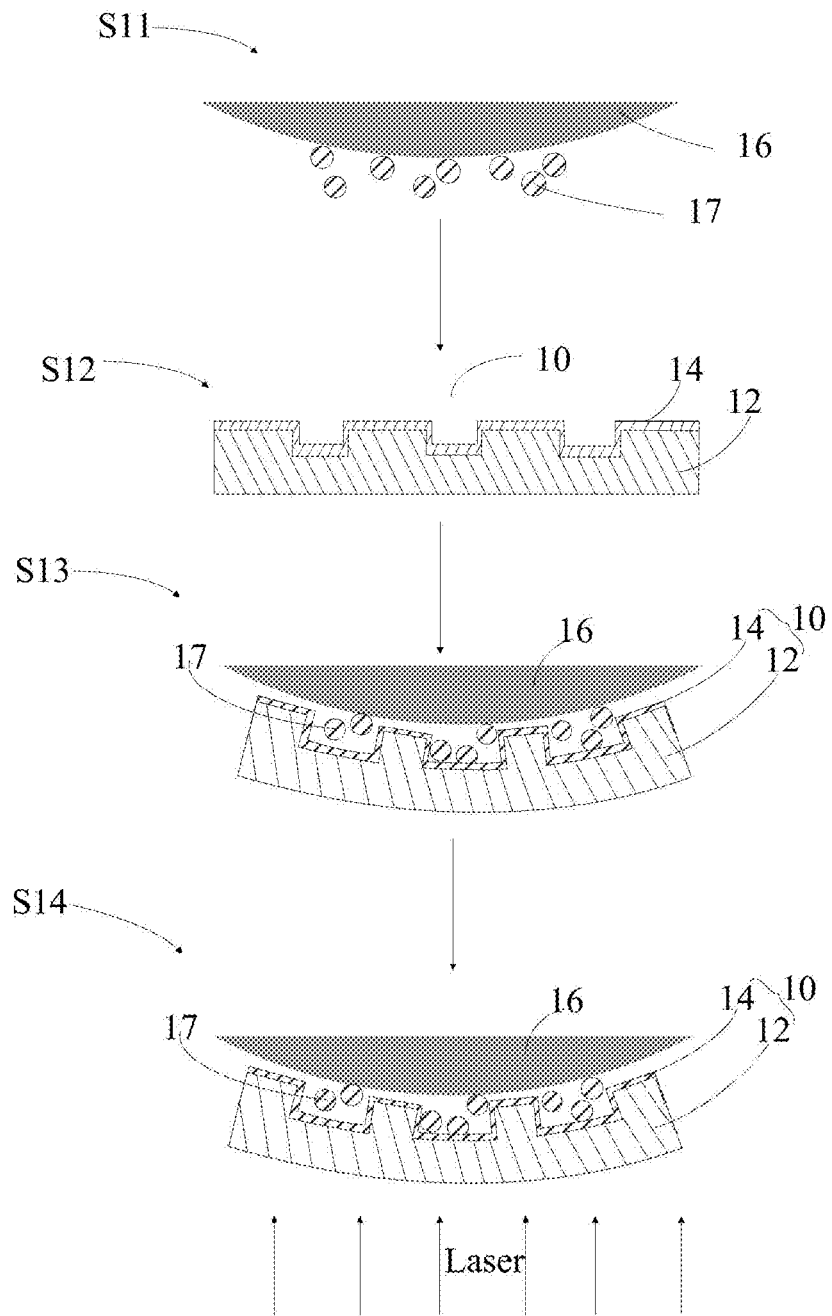
FIG. 14 is a flowchart of one embodiment of a method for detecting single molecules.

Referring to FIG. 14, a method for detecting single molecule of one embodiment may include the following steps:

step (S11), providing an object 16, the object 16 has the single molecules 17 dispersed on a surface of the object 16;

step (S12), providing the carrier 10 above;

step (S13), attaching the metal layer 14 of the carrier 10 on the surface of the object 16 so that the single molecules 17 is indirect contact with the metal layer 14;

step (S14), detecting the single molecules 17 with a detector.

In step (S11), the surface of the object 16 can be planar, curved, or any other shape. The object 16 can be an apple, tomato, or other fruit or vegetable. The single molecules 17 can be crystal violet (CV), 4-amino benzyl thiol (4-ATP), trans-1,2-bis(4-pyridyl)ethylene (BPE), pesticide residue such as imimide, methimide, or methyl parathion. In one embodiment, the single molecules 17 is crystal violet in a solution with a concentration from about $10^{-6}$M to about $10^{-8}$M.

In step (S13), the carrier 10 is a very flexible sheet and can be curved to have the same curvature as the surface of the object 16. In one embodiment, the metal layer 14 is indirect contact with the surface of the object 16 so that the single molecules 17 can be adhered to the metal layer 14. Furthermore, some solvent can be dipped or sprayed on the object 16 to dissolve the single molecules 17 to form a single molecule solution before attaching the metal layer 14 of the carrier 10 on the surface of the object 16. The single molecule solution is easy to be adhered to the metal layer 14. The solvent can exhaust the air between the object 16 and the carrier 10 so that the carrier 10 can be adhered to the surface of the object 16. The solvent can be water, ethanol, or propanol. In one embodiment, the solvent is water and dipped on the surface of the object 16 by a needle tube. The solvent can also be dipped or sprayed on the object 16 to dissolve the single molecules 17 to form a single molecule solution after attaching the metal layer 14 of the carrier 10 on the surface of the object 16.

Figure 15:
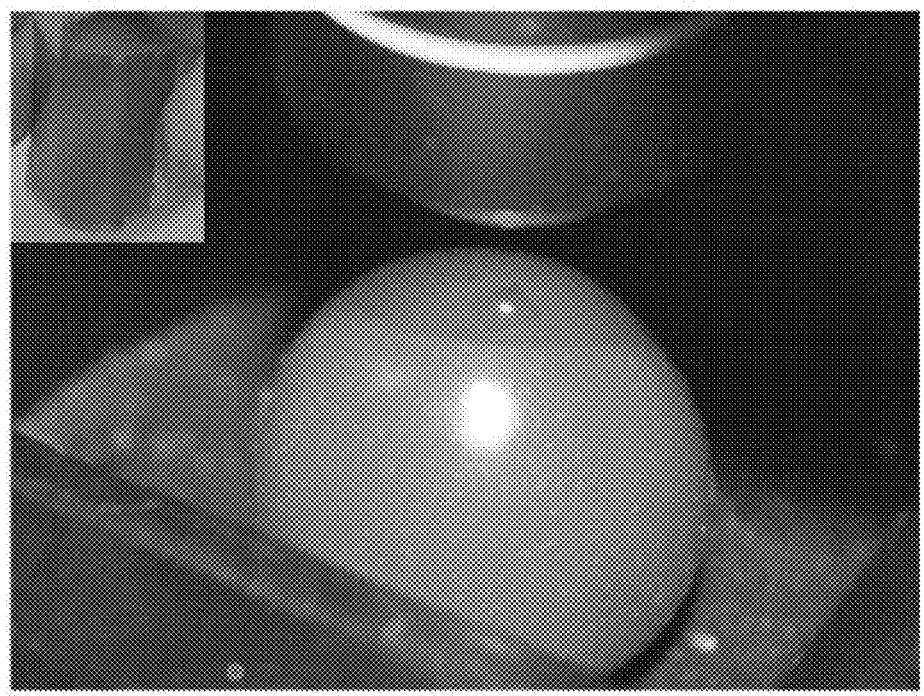
FIG. 15 is a picture of one embodiment showing a method for in situ detecting CV molecules of a tomato surface.
Figure 16:
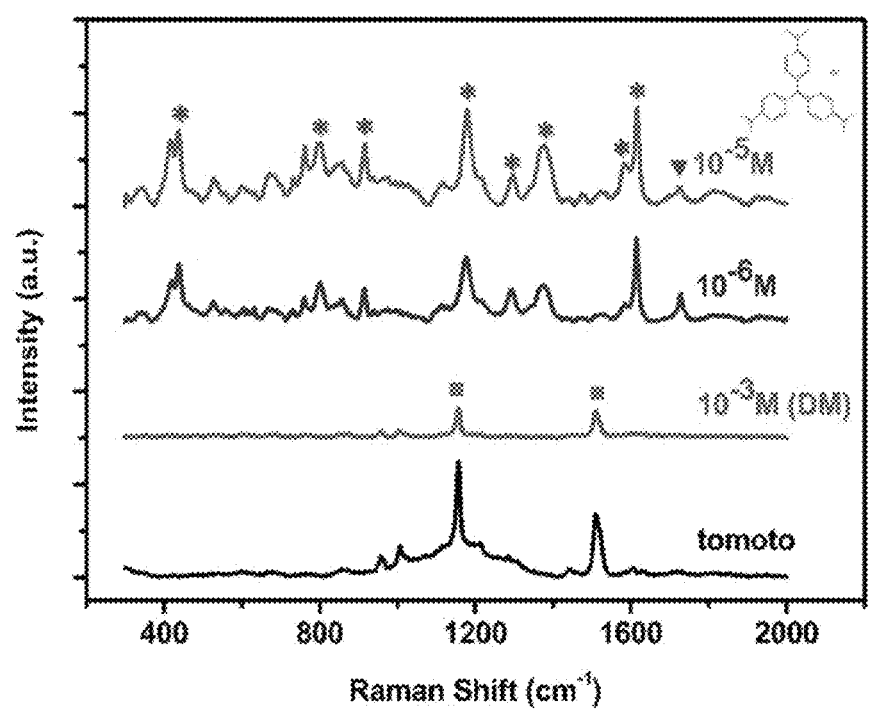
FIG. 16 is a Raman spectroscopy of CV molecules on the tomato surface obtained by the situ detecting of FIG. 15.

In step (14), a Raman Spectroscopy system is used to in situ detect the single molecules 17. In one embodiment, the Raman Spectroscopy system has an excitation source of He—Ne, an excitation wavelength of 633 nanometers, an excitation time of 10 seconds, a device power of 9.0 mW, and a working power of 0.1 mW. As shown in FIG. 15, the carrier 10 is kept in direct contact with the tomato object 16 and radiated by the Raman Spectroscopy system for about 30 seconds. The Raman laser radiates the carrier 10 from the side of the flexible substrate 12. FIG. 16 shows a Raman spectroscopy of Rhodamine molecules of the CV single molecules on the tomato detected by using the carrier 10.

Figure 17:
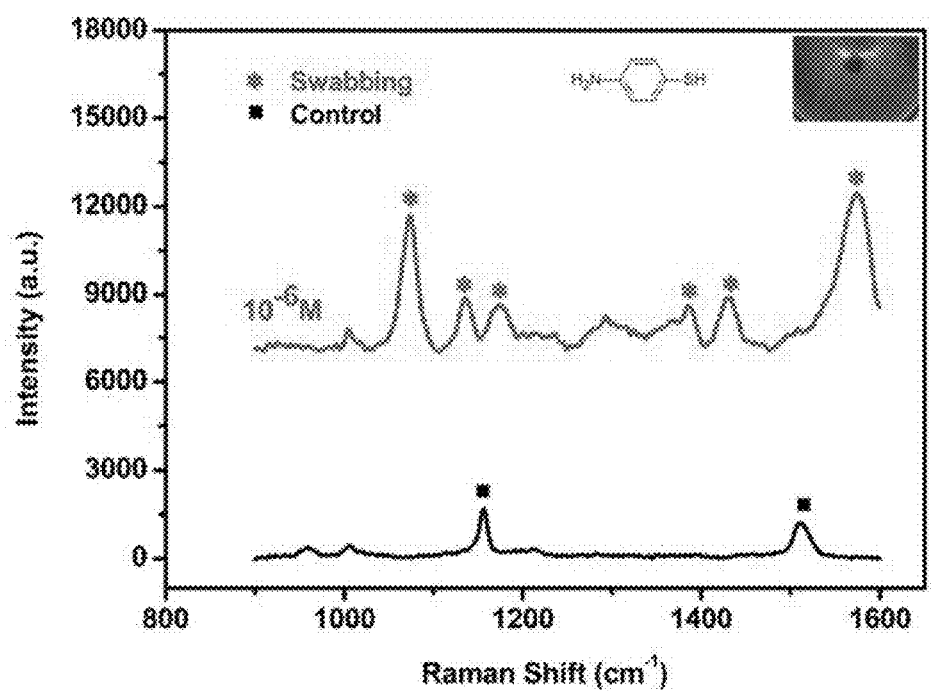
FIG. 17 is a Raman spectroscopy of 4-ATP molecules on the carrier obtained by wiping an apple surface using the carrier.

Alternatively, in step (S13), the carrier 10 can be used to wipe the outer surface of the object 16 first and then separated from the object 16. Thus, the single molecules 17 are adhered on the metal layer 14. In step (S14), Raman laser radiates the carrier 10 for 5 seconds from the side of the metal layer 14. FIG. 17 shows a Raman spectroscopy of Rhodamine molecules of the 4-ATP single molecules on the apple detected by using the carrier 10 to wipe the outer surface of the apple.

Figure 18:
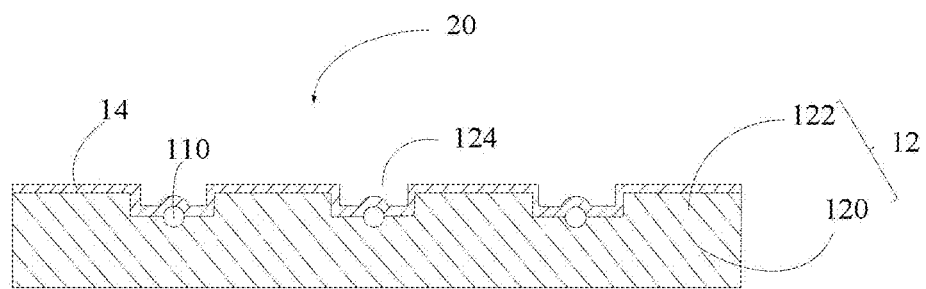
FIG. 18 is a schematic section view of another embodiment of a carrier for use in single molecule detection.

Referring to FIG. 18, a carrier 20 for use in single molecule detection of another embodiment is provided. The carrier 20 comprises a flexible substrate 12, a metal layer 14 located on the flexible substrate 12, and a carbon nanotube structure 110 sandwiched between the flexible substrate 12 and the metal layer 14. The flexible substrate 12 comprises a base 120 and a first bulge pattern 122 located on a surface of the base 120. The base 120 and the first bulge pattern 122 are integrated. The first bulge pattern 122 comprises a plurality of strip-shaped bulges 125 intersecting with each other to form a net and define a plurality of first recesses 124. The metal layer 14 is located on surfaces of the first bulge pattern 122. The carbon nanotube structure 110 is located on the bottom surface of the plurality of first recesses 124.

The carrier 20 is similar to the carrier 10 above except that the carbon nanotube structure 110. The carbon nanotube structure 110 can be a pure carbon nanotube structure or a carbon nanotube composite structure as discussed above.

Some carbon nanotubes of the carbon nanotube structure 110 are embedded in the flexible substrate 12, and some carbon nanotubes of the carbon nanotube structure 110 are embedded in the metal layer 14. The portion of the metal layer 14, that is on the carbon nanotube structure 110, form a third bulge pattern.

Figure 19:
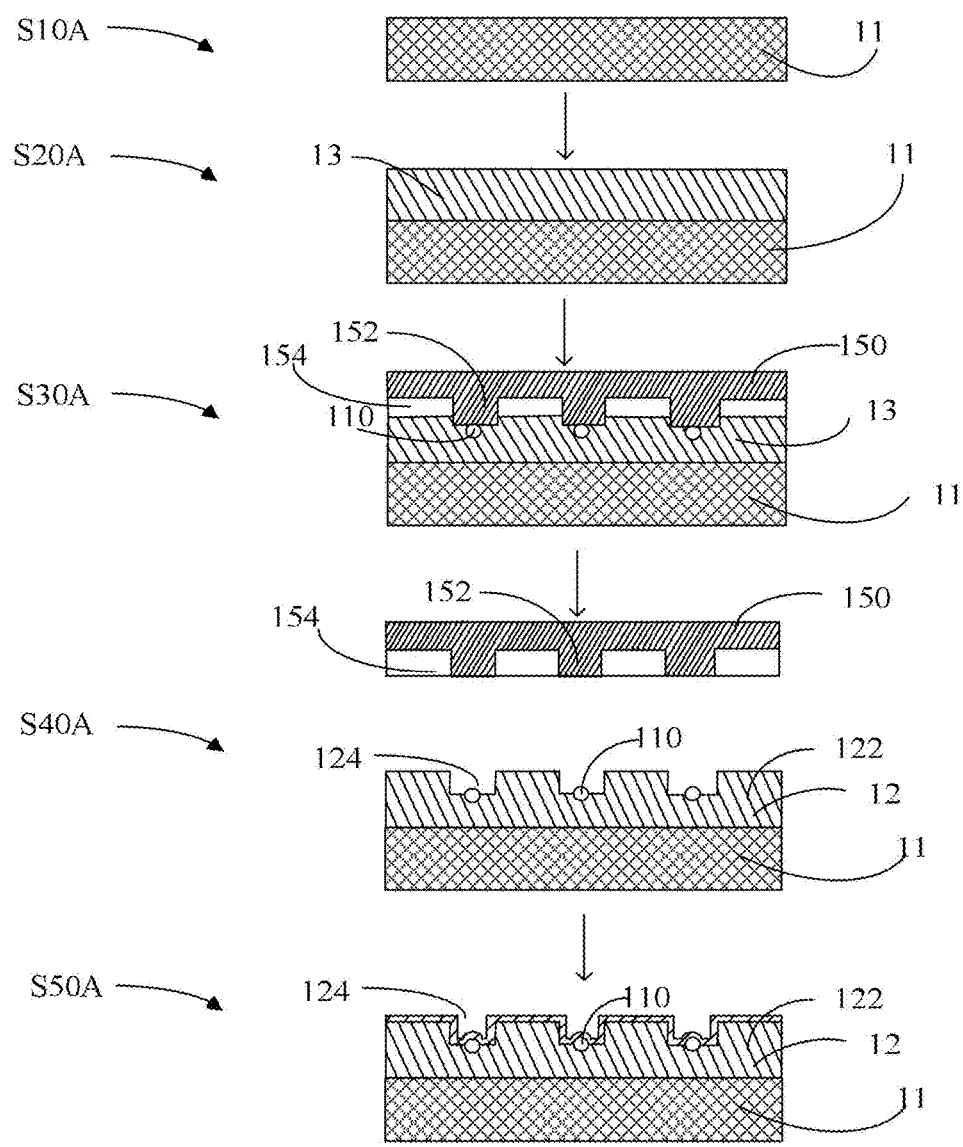
FIG. 19 is a flowchart of one embodiment of a method for making the carrier for use in single molecule detection of FIG. 18.

Referring to FIG. 19, a method for making the carrier 20 includes the following steps:

step (S10A), providing a rigid substrate 11;

step (S20A), coating a polymer layer 13 on a surface of the rigid substrate 11, wherein the polymer layer 13 is in semisolid state;

step (S30A), placing the carbon nanotube structure 110 on the second bulge pattern 152 of the template 150 and transferring the nano-scaled pattern of the template 150 on a surface of the polymer layer 13 by pressing the template 150 on the surface of the polymer layer 13;

step (S40A), obtaining the flexible substrate 12 by removing the template 150 and keeping the carbon nanotube structure 110 on the flexible substrate 12; and step (S50A), applying the metal layer 14 on the flexible substrate 12 to cover the carbon nanotube structure 110.

The method of FIG. 19 is similar to the method of FIG. 5, except that the carbon nanotube structure 110 is formed on the second bulge pattern 152 of the template 150 before pressing the template 150 on the surface of the polymer layer 13. In one embodiment, the template 150 is made by the method of FIG. 6 and the carbon nanotube structure 110 is kept on the second bulge pattern 152 after step (S304).

In one embodiment, the carbon nanotube structure 110 is a pure carbon nanotube structure including a carbon nanotube film. The carbon nanotube film includes a plurality of multi-walled carbon nanotubes arranged orderly. The plurality of multi-walled carbon nanotubes are etched to become thin and still kept on the second bulge pattern 152. The diameter of the plurality of multi-walled carbon nanotubes is smaller than the diameter of the width of the strip-shaped bulges. The carbon nanotube structure 110 can also includes a plurality of twisted carbon nanotube wires or untwisted carbon nanotube wires.

Because the polymer layer 13 is in semisolid state and has viscosity, the bonding force between the polymer layer 13 and the carbon nanotube structure 110 is greater than the bonding force between the template 150 and the carbon nanotube structure 110. Thus, the carbon nanotube structure 110 is kept on the polymer layer 13 after removing the template 150. The carbon nanotube structure 110 can increase the roughness of the bottom surface of the recesses 124. Thus, the SERS of the carrier 20 will be outstandingly enhanced. The carbon nanotube structure 110 can also increase the bonding force between the metal layer 14 and the flexible substrate 12. In the method of FIG. 6, the step of removing the carbon nanotube structure 110 can be omitted. Thus, the process of making the template 150 is simplified.

Figure 20:
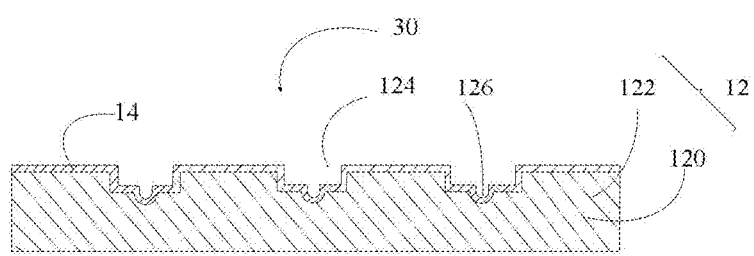
FIG. 20 is a schematic section view of another embodiment of a carrier for use in single molecule detection.

Referring to FIG. 20, a carrier 30 for use in single molecule detection of another embodiment is provided. The carrier 20 comprises a flexible substrate 12 and a metal layer 14 located on the flexible substrate 12. The flexible substrate 12 comprises a base 120 and a first bulge pattern 122 located on a surface of the base 120. The base 120 and the first bulge pattern 122 are integrated. The first bulge pattern 122 comprises a plurality of strip-shaped bulges 125 intersecting with each other to form a net and define a plurality of first recesses 124. The metal layer 14 is located on surfaces of the first bulge pattern 122.

The carrier 30 is similar to the carrier 10 above except that, a plurality of depressions 126 are formed on the bottom surface of the plurality of first recesses 124. The method for making the carrier 30 is similar to the method for making the carrier 20, except that, a plurality of depressions 126 are formed on the bottom surface of the plurality of first recesses 12 by removing the carbon nanotube structure 110 before applying the metal layer 14 on the first bulge pattern 122. The carbon nanotube structure 110 can be removed by ultrasonic method, or adhesive tape peeling, or oxidation.

Figure 21:
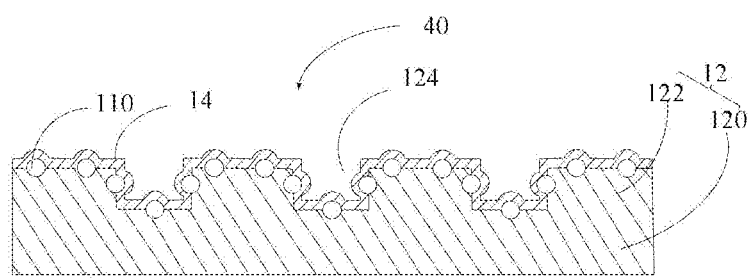
FIG. 21 is a schematic section view of another embodiment of a device for use in single molecule detection.

Referring to FIG. 21, a carrier 40 for use in single molecule detection of another embodiment is provided. The carrier 20 comprises a flexible substrate 12, a metal layer 14 located on the flexible substrate 12, and a carbon nanotube structure 110 sandwiched between the flexible substrate 12 and the metal layer 14. The flexible substrate 12 comprises a base 120 and a first bulge pattern 122 located on a surface of the base 120. The base 120 and the first bulge pattern 122 are integrated. The first bulge pattern 122 comprises a plurality of strip-shaped bulges 125 intersecting with each other to form a net and define a plurality of first recesses 124. The metal layer 14 is located on surfaces of the first bulge pattern 122.

The carrier 40 is similar to the carrier 20 above except that the carbon nanotube structure 110 is located on all the bottom surface of the plurality of first recesses 124, the side surface of the plurality of first recesses 124, and the top surface of the plurality of strip-shaped bulges 125.

Figure 22:
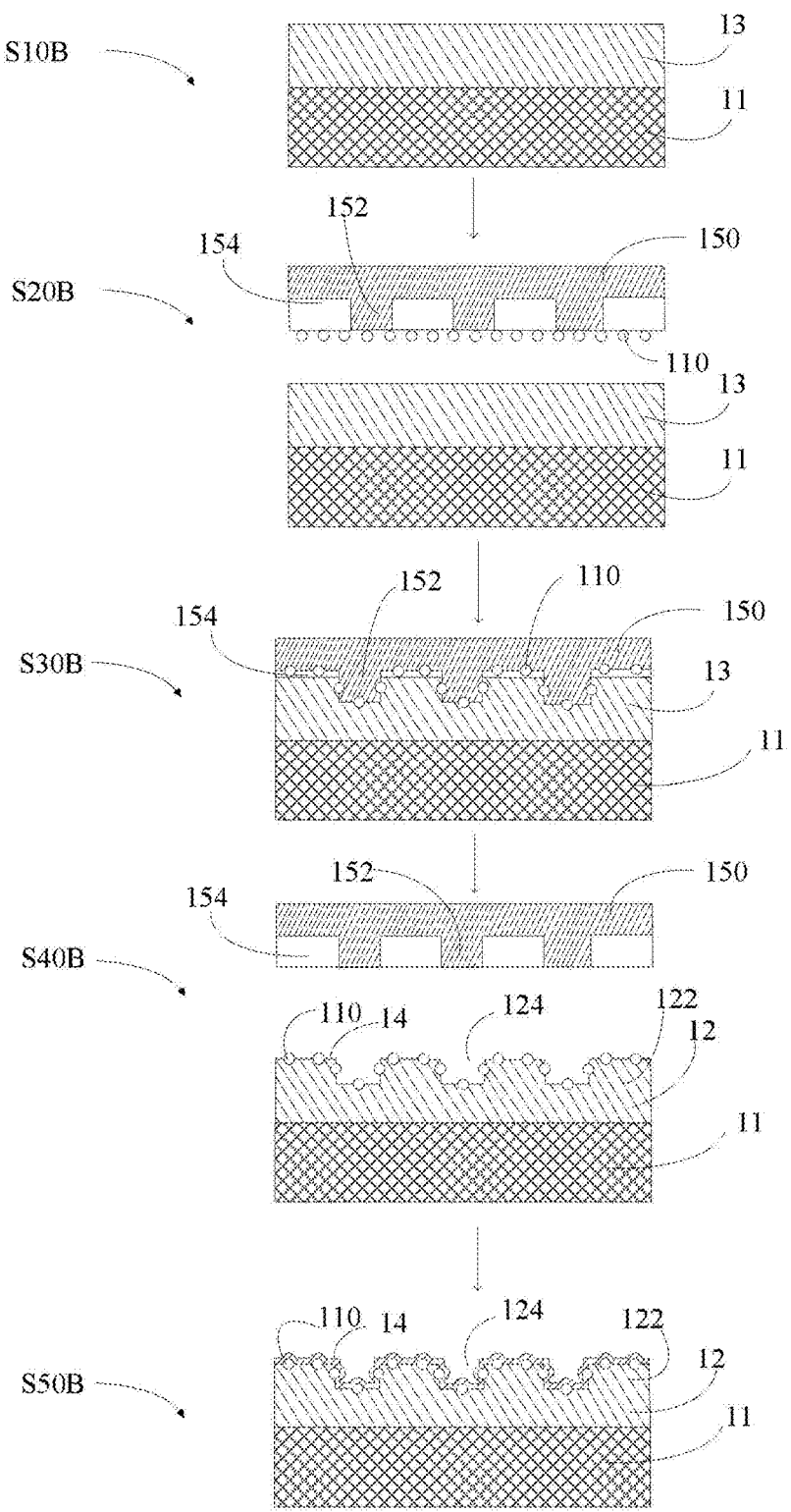
FIG. 22 is a flowchart of one embodiment of a method for making the carrier for use in single molecule detection of FIG. 21.

Referring to FIG. 22, a method for making the carrier 40 may include the following steps:

step (S10B), coating a polymer layer 13 on a surface of the rigid substrate 11, wherein the polymer layer 13 is in semisolid state;

step (S20B), placing the carbon nanotube structure 110 on the second bulge pattern 152 of the template 150 to cover entire surface of the template 150;

step (S30B), transferring the nano-scaled pattern of the template 150 on a surface of the polymer layer 13 by pressing the template 150 on the surface of the polymer layer 13;

step (S40B), obtaining the flexible substrate 12 by removing the template 150 and keeping the carbon nanotube structure 110 on the flexible substrate 12; and step (S50B), applying the metal layer 14 on the flexible substrate 12 to cover the carbon nanotube structure 110.

The method of FIG. 22 is similar to the method of FIG. 19, except that the carbon nanotube structure 110 covers entire surface of the template 15 in step (S20B). Alternatively, in step (S20B), the carbon nanotube structure 110 can be placed on the polymer layer 13 to cover entire surface of the polymer layer 13.

In step (S20B), carbon nanotube structure 110 can be attached on the template 15 by a binder or treating the carbon nanotube structure 110 using an solvent. The carbon nanotube structure 110 is located on all the bottom surface of the plurality of first recesses 124, the side surface of the plurality of first recesses 124, and the top surface of the plurality of first strip-shaped bulges 125. Thus, the SERS of the carrier 40 can be further enhanced.

Figure 23:
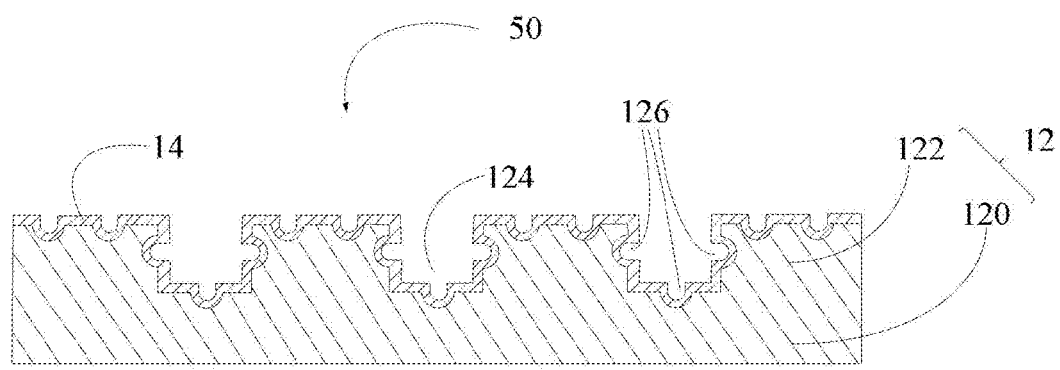
FIG. 23 is a schematic section view of another embodiment of a carrier for use in single molecule detection.

Referring to FIG. 23, a carrier 50 for use in single molecule detection of another embodiment is provided. The carrier 20 comprises a flexible substrate 12 and a metal layer 14 located on the flexible substrate 12. The flexible substrate 12 comprises a base 120 and a first bulge pattern 122 located on a surface of the base 120. The base 120 and the first bulge pattern 122 are integrated. The first bulge pattern 122 comprises a plurality of strip-shaped bulges 125 intersecting with each other to form a net and define a plurality of first recesses 124. The metal layer 14 is located on surfaces of the first bulge pattern 122.

The carrier 50 is similar to the carrier 30 above except that, a plurality of depressions 126 are formed on all the bottom surface of the plurality of first recesses 124, the side surface of the plurality of first recesses 124, and the top surface of the plurality of first strip-shaped bulges 125.

The method for making the carrier 50 is similar to the method for making the carrier 40 except that, a plurality of depressions 126 are formed on all the bottom surface of the plurality of first recesses 124, the side surface of the plurality of first recesses 124 and the top surface of the plurality of first strip-shaped bulges 125 by removing the carbon nanotube structure 110 before applying the metal layer 14 on the first bulge pattern 122.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for detecting single molecules on an object, comprising:

providing a carrier, wherein the carrier comprises a flexible substrate, and a metal layer located on the flexible substrate; the flexible substrate comprises a base and a bulge pattern located on a surface of the base, and the metal layer is located on the bulge pattern;

attaching the metal layer of the carrier on a surface of the object so that the surface of the object is indirect contact with the metal layer; and detecting the single molecules on the object with a detector.

2. The method of claim 1, wherein the bulge pattern comprises a plurality of strip-shaped bulges intersecting with each other to form a net and define a plurality of recesses.

3. The method of claim 2, further comprising a carbon nanotube structure located between the metal layer and the bulge pattern.

4. The method of claim 3, wherein the carbon nanotube structure is located on at least one of top surfaces of the plurality of strip-shaped bulges and bottom surfaces of the plurality of recesses.

5. The method of claim 4, wherein the carbon nanotube structure is a composite comprising a pure carbon nanotube structure and a protective layer coated on the pure carbon nanotube structure, and the pure carbon nanotube structure comprises a plurality of carbon nanotubes intersecting with each other.

6. The method of claim 5, wherein the protective layer comprises a material selected from the group consisting of metal, metal oxide, metal nitride, metal carbide, metal sulfide, silicon oxide, silicon nitride, and silicon carbide.

7. The method of claim 5, wherein the carbon nanotube structure comprises a first carbon nanotube film and a second carbon nanotube film stacked on each other, the first carbon nanotube film comprises a plurality of first carbon nanotubes joined end to end and arranged along a third direction, and the second carbon nanotube film comprises a plurality of second carbon nanotubes joined end to end and arranged along a fourth direction, the fourth direction different from the third direction.

8. The method of claim 2, further comprising a plurality of depressions located on the bulge pattern.

9. The method of claim 8, wherein the plurality of depressions is defined on at least one of top surfaces of the plurality of strip-shaped bulges and bottom surfaces of the plurality of recesses.

10. The method of claim 1, wherein the bulge pattern comprises a plurality of block-shaped bulges spaced apart from each other, arranged to form an array, and defines a plurality of grooves.

11. The method of claim 1, wherein the metal layer is a continuous structure and covers entire surface of the bulge pattern.

12. The method of claim 1, wherein the metal layer is a discontinuous structure.

13. The method of claim 1, wherein a thickness of the metal layer ranges from about 2 nanometers to about 200 nanometers.

14. The method of claim 1, wherein the metal layer comprises a material selected from the group consisting of gold, silver, copper, iron, nickel, and aluminum.

15. The method of claim 1, wherein the flexible substrate is a polymer sheet.

16. The method of claim 1, wherein a thickness of the flexible substrate ranges from about 10 micrometers to about 200 micrometers.

17. The method of claim 1, wherein the attaching the metal layer on the surface of the object comprises applying solvent between the object and the carrier.

18. The method of claim 1, wherein the attaching the metal layer on the surface of the object comprises wiping the surface of the object using the carrier first and then separating the carrier from the object.

19. The method of claim 18, wherein the detecting the single molecules with the detector comprises is performed after separating the carrier from the object.

20. The method of claim 1, wherein the detecting the single molecules with the detector is performed in situ by keeping the carrier on the surface of the object.

* * * * *